US012607627B2

(12) United States Patent (10) Patent No.: US 12,607,627 B2
King et al. (45) Date of Patent: Apr. 21, 2026

(54) USE OF MAGNETIC NANOPARTICLES FOR THE DETECTION AND QUANTITATION OF ANALYTE(S)

(71) Applicant: QUANTUM IP HOLDINGS PTY LIMITED, Chadstone (AU)

(72) Inventors: Paul Jeremy King, Melbourne (AU); Camden Yeung-Wah Lo, Melbourne (AU)

(73) Assignee: QUANTUM IP HOLDINGS PTY LIMITED, Chadstone (AU)

( * ) Notice: Subject to any disclaimer, the term of this patent is extended or adjusted under 35 U.S.C. 154(b) by 0 days.

(21) Appl. No.: 18/169,445

(22) Filed: Feb. 15, 2023

(65) Prior Publication Data

US 2023/0251249 A1 Aug. 10, 2023

Related U.S. Application Data

(60) Division of application No. 17/462,209, filed on Aug. 31, 2021, now Pat. No. 11,604,187, which is a continuation of application No. PCT/AU2021/050497, filed on May 25, 2021.

(30) Foreign Application Priority Data

May 25, 2020 (AU) ................................. 2020904881

(51) Int. Cl.
*G01N 33/543* (2006.01)
*G01N 33/553* (2006.01)

(52) U.S. Cl.
CPC . *G01N 33/54326* (2013.01); *G01N 33/54313* (2013.01); *G01N 33/553* (2013.01)

(58) Field of Classification Search
None
See application file for complete search history.

(56) References Cited

U.S. PATENT DOCUMENTS

| | | | |
|---|---|---|---|
| 2006/0205093 A1* | 9/2006 | Prins ........................ | C07K 1/22 436/526 |
| 2007/0197900 A1* | 8/2007 | Baudenbacher ............................ | G01N 33/54333 600/409 |
| 2009/0227044 A1* | 9/2009 | Dosev .............. | G01N 33/54333 436/526 |
| 2010/0213934 A1* | 8/2010 | Wang ...................... | G01N 27/72 324/252 |
| 2010/0253323 A1* | 10/2010 | De Theije ............ | G01N 21/552 324/204 |
| 2015/0072374 A1* | 3/2015 | Ng .......................... | C12M 47/04 435/287.1 |
| 2017/0022546 A1* | 1/2017 | Bashir .................. | C12Q 1/6825 |
| 2017/0261509 A1* | 9/2017 | Wang .............. | G01N 33/57488 |
| 2019/0351416 A1* | 11/2019 | Culbertson ......... | B01L 3/50273 |
| 2021/0002602 A1* | 1/2021 | Ludlam .................. | C12M 23/16 |

OTHER PUBLICATIONS

Choi et al., Automated Digital Microfluidic Platform for Magnetic-Particle-Based Immunoassays with Optimization by Design of Experiments, Anal. Chem. 2013, 85, pp. 9638-9646. (Year: 2013).*
Chung et al., Particles sorting in Micro Channel using designed Micro Electromagnetis of Magnetic Field Gradient, Journal of Magnetism and Magnetic Materials, 407, 2016, pp. 209-217. (Year: 2016).*

* cited by examiner

*Primary Examiner* — Gary Counts
(74) *Attorney, Agent, or Firm* — Dentons Bingham Greenebaum LLP; Brian W. Chellgren

(57) ABSTRACT

Described is a method and device for detecting an analyte in a sample, comprising bringing a sample comprising a target analyte into contact with magnetisable particles, the particles being coated with binding molecules complementary to the target analyte, resulting in bound and unbound binder complexes, positioning the magnetisable particles, comprising both bound and unbound binder complexes, in proximity to a magnetic field sensor, changing the magnetic field sufficient to release at least a portion of the magnetisable particles, comprising both bound and unbound binder complexes, from their proximity to the magnetic field sensor, and measuring changes in a magnetic signal detected from the net movement, being either translational or rotational movement, of the magnetisable particles relative to the magnetic sensor.

15 Claims, 2 Drawing Sheets

USE OF MAGNETIC NANOPARTICLES FOR THE DETECTION AND QUANTITATION OF ANALYTE(S)

CROSS-REFERENCE TO RELATED APPLICATIONS

This application is a divisional of U.S. application Ser. No. 17/462,209, filed Aug. 31, 2021, now U.S. Pat. No. 11,604,187, which is a continuation of international application no. PCT/US2021/050497, filed May 25, 2021, which claims the benefit of and priority to Australian Application No. 2020904881, filed May 25, 2020, all of which are expressly incorporated herein by reference.

FIELD OF THE INVENTION

The invention relates to a method for detecting an analyte(s) in a sample, and more specifically, the use of magnetisable nanoparticles and a magnetic sensor system. The invention also relates to a device for detecting analytes based on the use of magnetisable nanoparticles.

BACKGROUND OF THE INVENTION

There are many known methods to detect and quantify analytes in a sample. Such systems require an indirect method to quantify the analyte by detecting and measuring a complex that is bound to the analyte. Typically, such methods rely on a binding or recognition system whereby a visualisation aid is coated or linked to a binding molecule that binds to the analyte in the sample.

The binding molecule may include antibodies, enzymes or pharmacological agents that are specifically chosen based on their affinity for the target analyte. The molecule that directly binds the analyte may itself be labelled with an enzyme or a fluorophore (in the case of fluorescent labelling).

Alternately the molecule that directly binds the analyte may itself be unlabelled and is instead bound to a further binding agent that is itself labelled with an enzyme or fluorophore. This additional labelling procedure can amplify the signal and reduce background staining. A well-known complex is the avidin-biotin complex and the peroxidase-antiperoxidase technique.

Techniques for detecting and quantifying analytes in a sample need to be rapid, sensitive, qualitative and/or miniaturisable to fulfil the needs of in vitro diagnostics. Miniaturisation of devices can lead to slow and inefficient mixing of fluids due to an increase in viscous forces.

Point-of-care testing can reduce the turn-around time for diagnostic testing giving improved workflows and thus potentially aiding improved patient care. Such systems must include sensing technology to detect biomarkers (e.g. protein markers or nucleic acid markers). Magnetisable particles have been used for detecting analytes across manual assays for basic research to high throughput testing.

Many existing devices for detecting analytes attached to magnetisable particles require complex configurations that are unsuitable or are not easily adapted for miniaturisation in point-of-care testing applications.

The use of magnetisable particles relies on the functionalisation of the particles with binding molecules (e.g. antibodies with high affinity for the target analyte) to allow binding to the target analyte, followed by fluid exchange steps to achieve isolation and purification. It has been reported that the analyte capture rate scales with the total surface area of the suspended particles and therefore with the particle concentration. However, the use of a very high concentration of particles has disadvantages for downstream processes in an integrated multi-step lab-on-chip assay since high particle concentrations generally increase non-specific particle—particle and particle—surface interactions, enhance field-induced particle aggregation, cause steric hindrance in particle concentration steps, obstruct chemical reactions on the particles, and sterically hinder reactions between the particles and a biosensing surface.

Target analytes may be present in low concentrations within a sample, that also contains a high concentration of background material, such as blood or saliva. In such complex matrices, non-specific adhesion of non-targeted molecules to the magnetisable particles can reduce the effectiveness of the assay.

The process of magnetic particle-based capture of a target analyte consists of an encounter between the two components (the target analyte and the magnetic particle) and may rely upon the two components aligning their outer surfaces in a very specific manner relative to each other. Thus, the association rate of the two components may be limited by diffusion and by the geometric constraints of the two component's binding sites, and may also be reduced by the final chemical reaction.

Analytes can be captured in a flowing fluid or a static fluid. Without flow, a method that relies upon surface immobilised antibodies is limited by diffusion and can have a reduced binding rate.

After the capture of the target analyte by the magnetic particle, additional processing is required for detection. If used as a carrier only, the magnetisable particle is typically bound to identification molecules such as luminescent labels or fluorescent molecules. For accurate detection, it is important that only bound analytes are labelled, and that only bound labels are detected. This requires several washing or separation steps.

The magnetisable particles may also be used as a label to indicate binding of the target analyte at a sensing surface. Agglutination assays exploit a process wherein aggregates of particles are formed when specific analytes are present in the sample fluid. The degree of aggregation is a measure for the concentration of analytes within the fluid. The agglutination assays are demanding on the reagents because the assays are performed in one step without separation or stringency.

In magnetic agglutination assays, the formation of particle clusters is accelerated by bringing particles together under the influence of a magnetic field. An issue with such methodologies is that when the analyte concentration is much smaller than the magnetisable particle concentration, a small number of particle aggregates are formed, governed by Poisson statistics. Application of a magnetic field may be enhanced by applying a magnetic field during incubation. However, the magnetic field may also increase the non-specific binding between the particles. Non-specific binding (i.e. the bond is not mediated by the target analyte), results in a false positive signal. Non-specific binding can originate from several types of interactions such as van der Waals interactions, electrostatic interactions, and hydrophobic interactions causing background levels as well as statistical variations of the results, which therefore affect the limit of quantification and the precision of the method.

The use of magnetisable particles means that additional forces can be applied to the particles, for example, to separate bound from unbound particles.

An evaluation of the analytical performance of a detection methodology is based on the limit of quantification (LoQ) i.e. the lowest biomarker concentration that can be quantified with a given required precision.

Optimizing magnetisable particles for specific applications and selecting appropriate detection methods remain challenging for the magnetic nanotechnology community due to the increasing demands of detection sensitivity, molecular specificity, and application complexity.

The use of GMR in immunoassays has been used in a sandwich-type approach (such as an ELISA), where the molecular target is immobilised on the sensor surface with the addition of tagged magnetic probes (see Koh and Josephson "Magnetic nanoparticle sensors" *Sensors* 2009: 9; 8130-45 and Yao and Xu "Detection of magnetic nanomaterials in molecular imaging and diagnosis applications" *Nanotechnol. Rev* 2014: 3; 247-268).

Some techniques use superconducting quantum interference device (SQUID) to detect and measure Neel relaxation (misalignment of magnetic dipole) in magnetically labelled bacteria. In such techniques, a magnetic field is pulsed to cause magnetic dipole alignment and the subsequent dipole misalignment is detected.

It is an object of the present invention to address one or more of the abovementioned issues, and/or to provide a method for detecting an analyte in a sample and/or to at least provide the public with a useful choice.

SUMMARY OF THE INVENTION

In a first aspect there is described a method for detecting an analyte in a sample, comprising
   bringing a sample comprising a target analyte into contact
      with magnetisable particles, the particles being coated
      with binding molecules complementary to the target
      analyte, resulting in bound and unbound binder complexes,
   positioning the magnetisable particles, comprising both
      bound and unbound binder complexes, in proximity to
      a magnetic field sensor,
   changing the magnetic field sufficient to release at least a
      portion of the magnetisable particles, comprising both
      bound and unbound binder complexes, from their proximity to the magnetic field sensor, and
   measuring changes in a magnetic signal detected from the
      magnetisable particles as a result of the net movement
      (translational or rotational movement) of the magnetisable particles in relation to the magnetic sensor.
In a further aspect there is described a method for detecting an analyte in a sample, comprising
   providing sample testing device comprising
      a sample well or sample reservoir,
      one or more magnets for generating a magnetic field in
         the sample well or sample reservoir, and
      a magnetic field sensor for measuring changes over
         time in the magnetic field in the sample well or
         sample reservoir, and
   bringing a sample comprising a target analyte into contact
      with magnetisable particles within the sample well, the
      particles being coated with binding molecules complementary to the target analyte,
   positioning the magnetisable particles in proximity to the
      magnetic sensor,
   changing the magnetic field sufficiently to allow the
      magnetisable particles to move (translational or rotational movement) in relation to the magnetic sensor.

In a further aspect there is described a method for detecting an analyte, wherein the method:
   a) generates sufficient magnetic signal within 10 seconds
      to detect and/or measure an amount of target analyte in
      the sample, or
   b) has a limit of detection (LOD) of at least about 0.05
      pg/mL, or
   c) has a limit of quantification (LOQ) of at least about 0.1
      pg/mL, or
   d) one or more of (a) to (c).
In a further aspect there is described a device for detecting an analyte in a sample, comprising
   a sample well or sample reservoir,
   one or more magnets for generating a magnetic field in the
      sample well, and
   a magnetic field sensor for measuring changes over time
      in the magnetic field in the sample well, and
   wherein the one or more magnets and magnetic sensor are
adapted for use such that magnetic sensor can detect a change in the magnetic field based on the net movement (translational or rotational movement) of the magnetisable particles in relation to the magnetic sensor.

In a further aspect there is described a diagnostic system for detecting an analyte in a sample, the system comprising
   bringing a sample comprising a target analyte into contact
      with magnetisable particles, the particles being coated
      with binding molecules complementary to the target
      analyte,
   positioning the magnetisable particles in proximity to a
      magnetic field sensor,
   changing the magnetic field sufficient to release at least a
      portion of the magnetisable particles from their proximity to the magnetic field sensor, and
   measuring changes in a magnetic signal detected from the
      magnetisable particles as the magnetisable particles
      move (translational or rotational movement) in relation
      to the magnetic sensor, and
   wherein the diagnostic system is configured to
   a) acquire a sufficient magnetic signal within 20 seconds
      to detect and/or measure an amount of target analyte in
      the sample, or
   b) have a limit of detection (LOD) of at least about 0.05
      pg/mL, or
   c) have a limit of quantification (LOQ) of at least about
      0.1 pg/mL, or
   d) comprise one or more of (a) to (c).
   Any one or more of the following embodiments may relate to any of the above aspects.

In one configuration the device or diagnostic system acquires sufficient magnetic signal within 5, 10, 15 or 20 seconds to detect and/or measure an amount of target analyte in the sample, and suitable ranges may be selected from between any of these values.

In one configuration a magnetic field is applied to position the magnetisable particles in proximity to a magnetic field sensor.

In one configuration the magnetic field mixes the sample.

In one configuration the detection and quantitation of the analyte in the sample is dependent on the amount of magnetisable particles detected via a magnetic field sensor.

In one configuration the magnetisable particles are positioned using centrifugal force, acoustics or piezoelectricity.

In one configuration the magnetisable particles are functionalised with molecules that specifically bind to the analyte.

In one configuration the sample and magnetisable particles are processed by a microfluidic device. Preferably the microfluidic device facilitates binding between the magnetisable particles and analyte.

In one configuration the magnetic field promotes or enhances the binding of the magnetisable particles with the target analyte.

In one configuration the magnetisable particles are magnetic particles.

In one configuration the magnetisable particles are paramagnetic.

In one configuration the magnetisable particles are ferromagnetic.

In one configuration the detection is provided by a lab-on-chip device. Preferably the lab-on-chip device comprises a microfluidics device.

In one configuration the chip device has a multiplex chipset design.

In one configuration the magnetisable particles have an average particle size of about 5 to about 500 nm, and suitable ranges may be selected from between any of these values.

In one configuration the magnetisable particles have an average particle size of about 5, 10, 50, 100, 150, 200, 250, 300, 350, 400, 450 or 500 nm, and suitable ranges may be selected from between any of these values.

In one configuration the magnetisable particles have an average particle size of about 500, 550, 600, 650, 700, 750, 800, 850, 900, 950 or 1000 nm, and suitable ranges may be selected from between any of these values.

In one configuration the magnetisable particles have an average particle size of about 1000, 1500, 2000, 2500, 3000, 3500, 4000, 4500 or 5000 nm, and suitable ranges may be selected from between any of these values.

In one configuration the microfluidic device positions the magnetisable particles and analyte into close proximity with the magnetic sensor.

In one configuration the magnetisable particles and analyte are brought within 1, 10, 100, 500, 1000, 2000, 3000, 4000 or 5,000 μm from the sensing element of the magnetic sensor, and useful ranges may be selected between any of these values.

In one configuration the one or more magnets (or electromagnets) aligns the magnetisable particles.

In one configuration the one or more magnets generates a magnetic field that changes over time.

In one configuration the magnetic field generator can generate a continuity of magnitudes.

In one configuration the magnetic field generator can alternate the magnetic field between on and off.

In one configuration the magnetic field is generated and positioned in such a way as to maximise its effect on the magnetisable particles but minimise its effect on the magnetic sensor.

In one configuration the magnetic field sensor is adapted to maximise its sensing of the magnetisable particles and minimise the sensing from the magnet.

In one configuration the data acquisition by the sensor is synchronised with the microfluidic device, such that magnetic field signal from the sensor is identifiable as data from the sample when the microfluidic device has processed and positioned the magnetisable particles into close proximity with the magnetic sensor.

In one configuration data is continuously acquired from the sensor. Preferably data is acquired by the processing of signals from the magnetic sensor.

In one configuration acquired data is flagged as 1) environmental and/or ambient, or (2) test data. Preferably the categorisation of data to (1) environmental and/or ambient or (2) test data is dependent on the synchronisation of the data acquisition with the operation of the microfluidic device.

In one configuration the method is calibrated based on the synchronisation of the signal acquisition with the operation of the microfluidic device.

In one configuration the data is acquired over a period of about 1, 2, 3, 4, 5, 6, 7, 8, 9, 10, 20, 30, 40, 50, 60, 90 or 120 second(s), and useful ranges may be selected between any of these values.

In one configuration the signal output from the magnetic sensor is boosted by a signal amplifier.

In one configuration the signal output from the sensor is a voltage reading that is proportional to the magnetic field strength it senses.

In one configuration the voltage from the sensor is boosted in magnitude to a higher voltage, with all changes kept in proportion to the original signal, into a range that is compatible with data processing and collecting electronics.

In one configuration the amplified signal is converted from a voltage reading into digital bitstream and recorded by a computer.

In one configuration the conversion is performed by Analog to Digital Converter (ADC).

In one configuration the conversion rate or sampling rate can be 50-500,000 Hertz.

In one configuration the conversion resolution or sampling resolution can be 16-32 bit.

In one configuration the signal output is processed digitally with mathematical operations to generate a read out that can be used for interpretation and analysis.

In one configuration the use of the device, or diagnostic system, has a LOD of at least 0.05, 0.06, 0.07, 0.08, 0.09, 0.10, 0.15 or 0.20 pg/mL, and useful ranges may be selected between any of these values.

In one configuration the use of the device, or diagnostic system, has a LOD of at least 0.1 pg/mL.

In one configuration the use of the device, or diagnostic system, has a LOQ of at least 0.10, 0.11, 0.12, 0.13, 0.14, 0.15, 0.16, 0.17, 0.18, 0.19 or 0.20 pg/mL, and useful ranges may be selected between any of these values.

In one configuration the use of the device, or diagnostic system, has a LOQ of at least 0.1 pg/mL.

The term "comprising" as used in this specification means "consisting at least in part of". When interpreting statements in this specification which include that term, the features, prefaced by that term in each statement, all need to be present but other features can also be present. Related terms such as "comprise" and "comprised" are to be interpreted in the same manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7).

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.)

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

BRIEF DESCRIPTION OF THE FIGURES

The invention will now be described by way of example only and with reference to the drawings in which.

DETAILED DESCRIPTION

Figure 1:
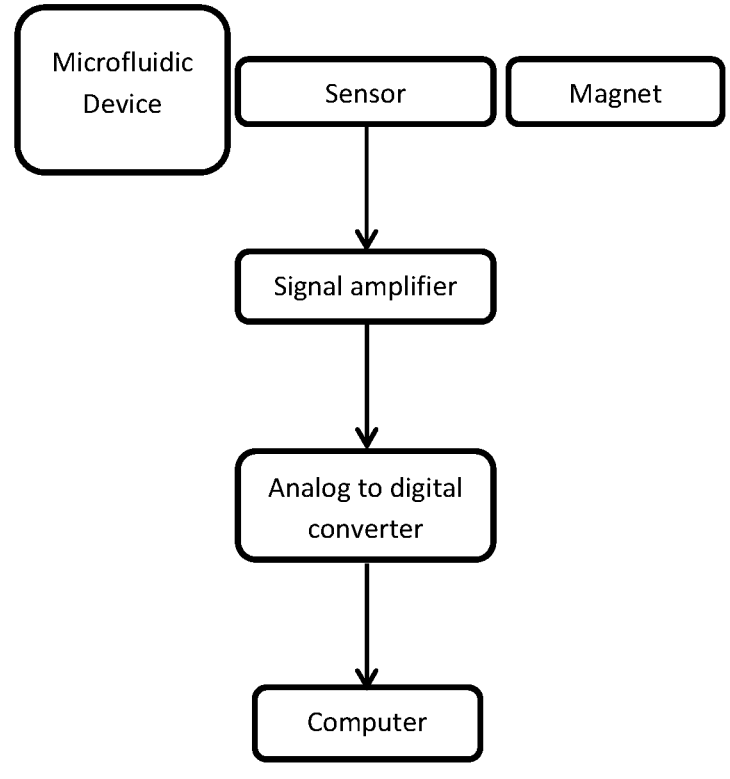
FIG. 1 is a flow diagram showing the setup of the method as described.

Described is a method for detecting an analyte in a sample, comprising the steps of:

bringing a sample comprising a target analyte into contact with magnetisable particles, the particles being coated with binding molecules complementary to the target analyte resulting in bound and unbound binder complexes, applying a magnetic field to position the magnetisable particles, comprising both bound and unbound binder complexes, in proximity to a magnetic field sensor (the 'capture' step), changing the magnetic field sufficient to release at least a portion of the magnetisable particles, comprising both bound and unbound binder complexes, from their proximity to the magnetic field sensor (the 'release' step), and measuring changes in a magnetic signal detected from the magnetisable particles as a result of the net movement of the magnetisable particles relative to the magnetic sensor. The movement is either translational or rotational movement.

The method described is based on the concept of bringing the magnetisable particles and analyte complex into close proximity with the magnetic field sensor. The magnetic field strength is modulated to allow the magnetisable particles and analyte complex to move (i.e. by translational or rotational movement) relative to the magnetic field sensor. The magnetic field sensor then measures changes in the magnetic field strength generated by the magnetisable particles over time due to Brownian rotation or diffusion that allows quantification of the amount of magnetisable particles-analyte complex, which then allows the amount of analyte to be determined in the sample. That is, the bound and unbound binder complexes are distinguished based on their diffusion characteristics. The magnetisable beads (i.e. both the bound and unbound complexes) physically move relative to the magnetic field sensor so that the bound and unbound complexes can be distinguished (given they will move to a differing degree due to different diffusion characteristics).

Broadly stated there may be three stages in the method of analysing a sample. The first stage may be a pre-sample baseline sensing stage. This stage is carried out to obtain a baseline reading without the sample present. The baseline reading provides a base comparison for the subsequent sample reading. The pre-sample baseline sensing stage may take 1, 2, 3, 4 or 5 seconds, and suitable ranges may be selected from between any of these values, (for example, about 1 to about 5, about 1 to about 4, about 2 to about 5, about 2 to about 3 or about 3 to about 5 seconds).

A second stage may be loading the sample into the device. This stage may include sample mixing and analyte-to-binding complexing (i.e. where the functionalised magnetisable particles bind to the analyte). This stage may take around 3, 4, 5, 6, 7 or 8 minutes, and suitable ranges may be selected from between any of these values, (for example, about 3 to about 8, about 3 to about 7, about 3 to about 5, about 4 to about 8, about 4 to about 6 or about 5 to about 8 minutes).

A third stage may be the sample read stage. That is, the magnetisable particles are positioned in proximity to a magnetic field sensor, the magnetic field is changed to release at least a portion of the bound and unbound binder complexes, and the magnetic sensor measures changes in the magnetic signal detected from the magnetisable particles as a result of their net movement relative to the magnetic sensor. This stage may take around 10, 11, 12, 13, 14, 15, 16, 17, 18, 19 or 20 seconds, and suitable ranges may be selected from between any of these values, (for example, about 10 to about 20, about 10 to about 18, about 10 to about 15, about 11 to about 20, about 11 to about 19, about 11 to about 16, about 11 to about 15, about 12 to about 20, about 12 to about 18, about 12 to about 15, about 13 to about 20, about 13 to about 19, about 13 to about 17 or about 13 to about 15 seconds).

As stated above, the amount of analyte in a sample is determined based on the change in the magnetic signal detected by the magnetic sensor. The magnetic sensor detects the change based on the net movement of the magnetisable particles. Once released from their proximity to the magnetic field sensor the magnetisable particles, comprising both bound and unbound binder complexes, will move away from the magnetic field sensor. This movement will be random based on Brownian diffusion.

Typically, the magnetic field sensor is located close to or adjacent (on the non-sample side) to the surface of the sample well or sample reservoir. When bound and unbound magnetisable particles are positioned in proximity to the magnetic field sensor, the bound and unbound magnetisable particles may locate at, or close to, the surface of wall of the sample well or sample reservoir until released. Once released from their proximity to the magnetic field sensor, the magnetisable particles may move, translationally or rotationally. Given their proximity to the surface of the sample well or sample reservoir, the bound and unbound magnetisable particles may typically move with a 180° freedom of movement relative to the surface of the sample well or sample reservoir. Brownian diffusion means that the magnetisable particles may move in any direction, including towards the magnetic field sensor. The magnetic signal detected by the magnetic field sensor is based on the net movement of the bound and unbound magnetisable particles.

Benefits of the present invention may include rapid detection (for example see Example 2) and a highly sensitive detection methodology (for example, see Examples 1 and 3).

When considering the encounter between the analyte and the magnetisable particle that are free in solution, the diffusional encounter step can be split up into (1) the process of diffusional transport through the fluid volume, and (2) the process of near-surface alignment. Where volume transport generates the first encounters between particles and target analyte, the subsequent near-surface alignment process deals with the alignment rate of the binding sites of the reactants. The volume transport is essentially a translational process, while the alignment is determined by both the translational and the rotational mobility of the reactants.

When the free components react in solution, the alignment process (i.e. rotational diffusion) is an important restriction due to the highly specific alignment constraints, but volume transport (i.e. translational diffusion) is not a limitation. In the case when one of the components is attached to a surface, volume transport can become a limitation.

The magnetic properties of nano- and micron-sized magnetic materials differ from those of the corresponding bulk magnetic materials. Typically, magnetisable particles are classified as paramagnetic, ferromagnetic, ferrimagnetic, antiferromagnetic, or superparamagnetic based on their magnetic behaviour in the presence and absence of an applied magnetic field.

Diamagnetic materials exhibit no dipole moment in the absence of a magnetic field, and in the presence of a magnetic field they align against the direction of the magnetic field.

Paramagnetic particles exhibit random dipole moments in the absence of a magnetic field, and in the presence of a magnetic field they align with the direction of the magnetic field.

Ferromagnetic materials exhibit aligned dipole moments.

Ferrimagnetic and antiferromagnetic materials exhibit alternating aligned dipole moments.

In one embodiment the magnetisable particles are paramagnetic particles. Such particles will become magnetic when subjected to a magnetic field. Once the magnetic field is removed, the particles will begin to lose their magnetic characteristics.

In an alternate embodiment the magnetisable particles are ferromagnetic particles. That is, they always exhibit magnetic characteristics regardless of whether subjected to a magnetic field.

Commercially available magnetisable particles include Dynaparticles M-270, Dynaparticles M-280, Dynaparticles MyOne T1, and Dynaparticles MyOne C1 from Thermo Fisher Scientific, μMACS MicroParticles from Miltenyi Biotec, SPHERO™ Superparamagnetic Particles, SPHERO™ Paramagnetic Particles, and SPHERO™ Ferromagnetic Particles from Spherotech.

The magnetisable particles may be formed by ferrites which are themselves formed from iron oxide (such as magnetite and maghemite). Various methods are known for synthesising iron oxide and metal-substituted ferrite magnetisable particles such as co-precipitation, thermal decomposition, and hydrothermal. Co-precipitation processes use stoichiometric amounts of ferrous and ferric salts in an alkaline solution in conjunction with a water-soluble surface coating material, such as polyethylene glycol (PEG), where the coating provides colloidal stability and biocompatibility. The size and properties of the magnetisable particle can be controlled by adjusting the reducing agent concentration, pH, ionic strength, temperature, iron salts source, or the ratio of $Fe^{2+}$ to $Fe^{3+}$.

The size and shape of magnetisable particles can be tailored by varying the reaction conditions, such as the type of organic solvent, heating rate, surfactant, and reaction time. This method leads to narrow size distributions of the magnetisable particles in the size range 10 to 100 nm. Fe' may be substituted by other metals to boost the saturation magnetisation.

The magnetisable particles may be coated with a hydrophobic coating during the synthesis process. If so, then the method of manufacturing the magnetisable particles may include an additional step of ligand exchange so that the magnetisable particles can be dispersed in water for further uses.

The magnetisable particles may be manufactured by polyol-hydrothermal reduction which produces water-dispersed magnetisable particles in the size range from tens to several hundred nanometres. The size and surface-functionalisation of the iron oxide magnetisable particles may be optimised by adjusting the solvent system, reducing agent, and type of surfactant used. This process may be used to synthesise FePt magnetisable particles.

The magnetisable particles may be manufactured by a reverse water-in-oil micelle methodology. This method forms a microemulsion of aqueous nanodroplets of iron precursors that is stabilized by a surfactant in the oil phase with the magnetic nanoparticles obtained by precipitation. Iron oxide nanocrystals may be assembled by combining the microemulsion and silica sol-gel, which may be obtained via co-precipitation into magnetisable particles having a diameter of more than 100 nm.

Metallic magnetisable particles may be either monometallic (e.g., Fe, Co, or Ni) or bimetallic (e.g., FePt and FeCo). Alloy magnetisable particles may be synthesised by physical methods including vacuum-deposition and gas-phase evaporation. These methods may produce FeCo magnetisable particles with high saturation magnetisation (about 207 emu/g) and may be synthesised via the reduction of $Fe^{3+}$ and $Co^{2+}$ salts.

The magnetisable particles may comprise a single metallic or metallic oxide core. The magnetisable particles may comprise multiple cores, multilayers of magnetic materials and nonmagnetic materials. The magnetisable particles may comprise a coating of silica or polymer cores with magnetic shells. The nonmagnetic core particles may comprise silica or other polymers.

The magnetisable particles may comprise a dielectric silica core coated with a magnetic shell. The magnetic shell may be formed from Co, FePt, or $Fe_3O_4$. The shell may also comprise a stabiliser such as silica shell or polyelectrolyte layer. The magnetisable particles may be mesoporous magnetisable particles.

The coating on the magnetisable particle may define the interactions between the magnetisable particles and biological molecules (such as analytes) and their biocompatibility. The coating can be used to define the surface charge, which together with the coating may alter the hydrodynamic size of the magnetic particle. The hydrodynamic size of the magnetisable particle may alter the functionality of the magnetic particle.

The magnetisable particles may be coated with specific coatings that provide forces of electrostatic and steric repulsion. Such coatings may assist stabilisation of the magnetisable particles which may prevent agglomeration or precipitation of the magnetisable particles.

The magnetisable particles may comprise of a coating formed from inorganic materials. Such magnetisable particles may be formed with a core-shell structure. For example, a magnetisable particle coated by biocompatible silica or gold (e.g. alloy magnetic nanoparticles, FeCo and CoPt coated with silica). The shell may provide a platform to modify the magnetisable particles with ligands (e.g. thiols). Other inorganic coating materials may include titanate or silver. For example, silver-coated iron oxide magnetisable particles may be synthesised and integrated with carbon paste.

The shell may be formed from silica. A benefit of coating with silica is the ability of the silica-coated magnetisable particles to bind covalently with versatile functional molecules and surface-reactive groups. The silica shell may be manufactured, for example, by the Stober method using sol-gel principles or the Philipse method or a combination thereof. The core of the magnetisable particle may be coated with tetraethoxysilane (TEOS), for example, by hydrolysis of TEOS under basic conditions which condenses and polymerises TEOS into a silica shell on the surface of the magnetic core. A cobalt magnetisable particle may be coated using a modified Stober method that combines 3-aminopropyl)trimethoxysilane and TEOS.

The Philipse method forms a silica shell of sodium silicate on the magnetic core. A second layer of silica may be deposited by the Stober method. The reverse microemulsion method may be used to coat with silica. This method may be used with surfactants. The surfactant may be selected from Igeoal CO-520 to provide a silica shell thicknesses of about 5 to about 20 nm. Preferably the reagents for manufacturing silica shells is selected from amino-terminated silanes or alkene-terminated silanes. Preferably the amino-terminated silanes is (3-aminopropyl)trimethoxysilane (APTMS). Preferably the alkene-terminated silanes is 3-methacryloxypropyl)trimethoxylsilane.

The magnetisable particles may be coated with gold. Gold-coated iron oxide nanoparticles may be synthesised by any one of chemical methods, reversed microemulsion, and laser-promoted methods. Gold-coated magnetisable particles may be synthesised by directly coating gold on the magnetisable particle core. Alternately, the gold-coated magnetisable particle may be synthesised by using silica as an intermediate layer for the gold coating. Preferably reduction is used method to deposit gold shells on the magnetisable particles.

Metal oxide or silica-coated magnetic cores may first be functionalized with 3-aminopropyl)trimethoxysilane prior to the electrostatically attachment of about 2 to about 3 nm gold nanocrystal seeds (from chloroauric acid) to the surface followed by the addition of a reducing agent to form the gold shell. Preferably the reducing agent is a mild reducing agent selected from sodium citrate or tetrakis(hydroxymethyl) phosphonium chloride. In some embodiments the gold shell is formed from reduction of gold(III) acetate $(Au(OOCCH_3)_3)$. In some embodiments the gold shells are formed on metallic magnetic cores (e.g. nickel and iron) by reverse micelles.

The magnetisable particles may be functionalised with organic ligands. This may be performed in-situ (i.e. functional ligands provided on the magnetisable particle during the synthesis step), or post-synthesis. The magnetisable particles may be functionalised with terminal hydroxyl groups (—OH), amino groups (—NH$_2$), and carboxyl groups (—COOH). This may be achieved by varying the surfactant (e.g., dextran, chitosan, or poly(acrylic acid)) used in the hydrothermal synthesis.

The functionalisation of the magnetisable particle post-synthesis may allow for the functionalisation of customised ligands on any magnetisable particle surface. Post-synthesis functionalisation may be carried out by ligand addition and ligand exchange. Ligand addition comprises the adsorption of amphiphilic molecules (that contain both a hydrophobic segment and a hydrophilic component) to form a double-layer structure. Ligand-exchange replaces the original surfactants (or ligands) with new functional ligands. Preferably the new ligands contain a functional group that is capable of binding on the magnetisable particle surface via either strong chemical bonding or electrostatic attraction. In some embodiments the magnetisable particle also includes a functional groups for stabilisation in water and/or bio-functionalisation.

The magnetisable particles may be coated with ligands that enhance ionic stability. The functional groups may be selected from carboxylates, phosphates, and catechol (e.g. dopamine). The ligand may be a siloxane group for coating of surfaces enriched in hydroxyl groups (e.g. metal oxide magnetic particle or silica-coated magnetic particles). The ligand may be a small silane ligand that links the magnetisable particle and various functional ligands (e.g. amines, carboxylates, thiols, and epoxides. The silane ligand may be selected from N-(trimethoxysilylpropyl)ethylene diaminetriacetic acid and (triethoxysilylpro-pyl)succinic anhydride to provide a carboxylate-terminated magnetic particles. The functional groups may be selected from phosphonic acid and catechol (to provide hydrophilic tail groups). The functional groups may be selected from amino-terminated phosphonic acids. Functional groups may be selected from 3-(trihydroxysilyl)propyl methylphosphonate for dispersion in aqueous solution. The ligand may be selected from dihydroxyhydrocinnamic acid, citric acid, or thiomalic acid for magnetisable particles for dispersion in water.

In some embodiments the magnetisable particle is functionalised with polymeric Ligands. The polymer may be selected from natural polymers (e.g. starch, dextran or chitosan), PEG, polyacrylic acid (PAA), poly(methacrylic acid) (PMAA), poly(N,N-methylene-bisacrylamide) (PMBAm), and poly(N,N/-methylenebisacrylamide-co-glycidyl methacrylate) (PMG).

The functional group on the magnetisable particle surface serves as a linker to bind with a complementary biomolecules. The biomolecules may be a small biomolecules. The small biomolecule may be selected from vitamins, peptides, and aptamers. The biomolecule may be a larger biomolecule. The larger biomolecule may be selected from DNA, RNA and proteins.

In relation to nucleic acid attachment, the nucleic acid may be conjugated by non-chemical methods (e.g. electrostatic interaction) or chemical methods (e.g. covalent bonding). The nucleic acid chain may be modified with functional groups. The functional groups may be selected from thiols or amines, or any combination thereof.

The conjugation of larger biomolecules may rely on their specific binding interaction with a wide range of subtracts and synthetic analogues, such as specific receptor-substrate recognition (i.e. antigen-antibody and biotin-avidin interactions).

A specific pair of proteins may be used to immobilise species on the magnetic particle. Physical interactions include electrostatic, hydrophilic-hydrophobic, and affinity interactions.

In some embodiments the biomolecule has a charge opposite to that of the magnetic polymer coating (e.g. polyethylenimine or polyethylenimine). For example, a positively charged magnetisable particle binding with negatively charged DNA.

The magnetisable particle may utilise the biotin-avidin interaction. The biotin molecules and tetrameric streptavidin have site-specific attraction with low nonspecific binding for controlling the direction of interacted biomolecules, such as the exposure of the Fab region of an antibody toward its antigen.

The magnetisable particle may bind to biomolecules using covalent conjugation. The covalent conjugation may be selected from homobifunctional/heterobifunctional cross-linkers (amino group), carbodiimide coupling (carboxyl group), maleimide coupling (amino group), direct reaction (epoxide group), maleimide coupling (thiol group), schiff-base condensation (aldehyde group), and click reaction (alkyne/azide group).

The magnetisable particles may have an average particle size of about 5, 10, 50, 100, 150, 200, 250, 300, 350, 400, 450 or 500 nm, and suitable ranges may be selected from between any of these values, (for example, about 5 to about 500, about 5 to about 400, about 5 to about 250, about 5 to about 100, about 5 to about 50, about 10 to about 500, about 10 to about 450, about 10 to about 300, about 10 to about 150, about 10 to about 50, about 50 to about 500, about 50 to about 350, about 50 to about 250, about 50 to about 150, about 100 to about 500, about 100 to about 300, about 150 to about 500, about 150 to about 450 or about 200 to about 500 nm).

The magnetisable particles may have an average particle size of about 500, 550, 600, 650, 700, 750, 800, 850, 900, 950 or 1000 nm, and suitable ranges may be selected from between any of these values, (for example, about 500 to about 1000, about 500 to about 850, about 500 to about 700, about 550 to about 1000, about 550 to about 800, about 600 to about 1000, about 600 to about 900, about 650 to about 1000, about 650 to about 950, about 650 to about 800 or to about 700 to about 1000 nm).

The magnetisable particles may have an average particle size of about 1000, 1500, 2000, 2500, 3000, 3500, 4000, 4500 or 5000 nm, and suitable ranges may be selected from between any of these values, (for example, about 1000 to about 5000, about 1000 to about 4000, about 1500 to about 5000, about 1500 to about 4500, about 1500 to about 3500, about 2000 to about 5000, about 2000 to about 4000, about 2500 to about 5000, about 2500 to about 3500, about 3000 to about 5000 nm).

The variation in the particle size of the magnetisable beads may be less than 10, 9, 8, 7, 6, 5, 4, 3, 2 or 1%, and suitable ranges may be selected from between any of these values.

Microfluidics enable faster analysis and reduced response times. Microfluidic systems also offer the ability to automate the preparation of the sample, thereby reducing the risk of contamination and false positives by human error. Additionally, microfluidic systems require low sample volumes. Microfluidics may reduce diffusional distances by increasing the surface area to volume ratios, reducing reagent consumption through micro- and nanofabricated channels and chambers, and/or automating all steps of the process.

Microfluidics allows for miniaturisation which allows for lab-on-chip applications. Microfluidics may be used as part of the biosensor, for example, including channels for acquiring a biological sample (e.g., saliva and/or Gingival Crevicular Fluid), processing the fluid (e.g., combining with one or more reagents and/or detecting an interaction with a biomolecule, etc.)

The microfluidics may require some degree of sample preparation. The sample preparation may include cell lysis, washing, centrifugation, separation, filtration, and elution. In some embodiments the sample preparation is prepared off-chip. In an alternative sample preparation is prepared on-chip.

In some configurations the microfluidics system includes hard or flexible materials, and may include electronics that may be integrated into the device. The electronics may include wireless communication electronics.

The microfluidic system may be a flow-through or stationary system. For example, the microfluidic system may comprise magnetic field sensor that is stationary relative to the microfluidic system.

The microfluidic system may operate passively. For example, the microfluidic system may operate under passive diffusion. That is, the microfluidic system does not require flow generated actively to perform effectively.

The microfluidic system may include a network of reservoirs, and that may be connected by microfluidics channels. The microfluidics channels may be configured for active metering or passive metering. This may allow for sample fluid to be drawn into the microfluidics channel and passed into a sample chamber.

The microfluidic system may include microfluidic channels that are configured to allow access to various sample and/or detection regions on the device at various times. For example, the microfluidics device integrated into or on an aligner may be configured to provide timing via temporal-sampling of a fluid. For example, a microfluidic system can be designed to enable sampling with chronological order and controlled timing. In some variations, the timing of fluid within the microchannel may be timed actively, e.g., by the opening of a channel via release of a valve (e.g. an electro-mechanical valve, an electromagnetic valve, a pressure valve). Examples of valves controlling fluid in a microfluidic network include piezoelectric, electrokinetics and chemical approaches.

The microfluidics may include a plurality of microfluidics channels that are sequentially arranged. The fluid may be drawn into the microfluidics at a metered rate. The timing of access of samples to the channels may be staggered.

The device may carry out signal multiplexing. That is the device may be used to sample and/or measure multiple biomarkers in controlled intervals. For example, the device may be used to provide access to one or more sample chambers. The device may include one or more valves that are controlled by control circuitry in the device. The one or more valves may be connected to each other. Thus, the device may be adapted to perform simultaneous detection of multiple analytes in a common sample body. Additionally or alternatively, the device may be configured to perform simultaneous multiple detection of multiple samples of the same target.

The microfluidic channel(s) may have a cross section in the range of about 0.001 to 0.01 mm$^2$, 0.01 to 0.1 mm$^2$, 0.1 to 0.25 mm$^2$, 0.25 to 0.5 mm$^2$, 0.1 to 1 mm$^2$, 0.5 to 1 mm$^2$, 1 to 2 mm$^2$, or 2 to 10 mm$^2$, and useful ranges may be selected between any of these values.

In some embodiments the microfluidics receives a predetermine sample volume in the range of about 0.1 to 1 μL, 1 to 5 μL, 5 to 10 μL, 10 to 20 μL, or 20 to 50 μL or more, and useful ranges may be selected between any of these values.

Figure 2:
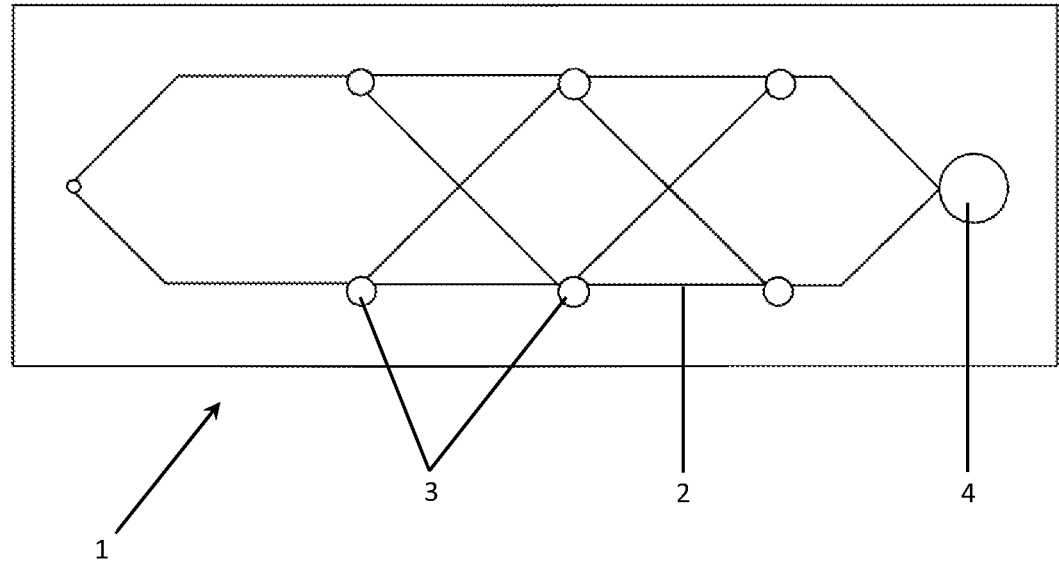
FIG. 2 is a diagrammatic representation of a microfluidics device.

Shown in FIG. 2 is an example of a microfluidic device 1. The microfluidic device 1 may comprise a plurality of channels 2 arranged to direct liquid and particle flow towards sensors 3 from the sample insertion area 4.

The channels may have a cross-sectional dimension as mentioned above, and more preferably of about 0.1 mm$^2$ (0.1 mm×1.0 mm). The channels may have a variable length. For example, the channels may be 1, 5, 10, 15, 20, 25, 30, 35, 40, 45, 50, 60, 70, 80, 90, 100, 120, 140, 160, 180, 200, 250, or 300 mm long, and useful ranges may be selected between any of these values, (for example, from about 1 to 10, 1 to 20, 1 to 50, 1 to 100, 1 to 200, 1 to 300, 10 to 20, 10 to 40, 10 to 60, 10 to 80, 10 to 100, 50 to 100, 50 to 150, 50 to 200, 50 to 250, 50 to 300, 100 to 200, or 100 to 300 mm long).

The above dimensions of the channels facilitate passive capillary flow.

When in use, a sample is introduced to the microfluidics device 1 via the sample insertion area 4.

In some embodiments, a filter membrane may be present at the insertion area 4 to separate and allow through the desired components of a sample. For example, to allow plasma from blood to pass into the microfluidics device 1, but not cells. The presence of the filter membrane is dependent on the nature of the sample, and whether it comprises components for which it is desirable that they do not pass into the microfluidics device 1.

Once introduced into the insertion area 4, the sample will then contact the microfluidic channels 2 and flow through the rest of the channel circuit.

The microfluidic device 1 may comprise of one or more magnetic sensors 3 in close proximity to the channels 2. For example, the microfluidic device 1 may comprise 1, 2, 3, 4, 5, 6, 7, 8, 9, or 10 magnetic sensors arrayed around the microfluidic device 1. As shown in FIG. 5, the microfluidic device 1 comprises six magnetic sensors (6) located at the channel 2 juncture points.

In one embodiment the microfluidic device 1 comprises two or more magnets, such as permanent magnets or electromagnets for example, arranged in close proximity to the channels that can be activated to draw magnetisable particles through the liquid in the channels 2 to enhance mixing. The mixing may, for example, be carried out for 1, 2, 3, 4, 5, 6, 7, 8, 9 or 10 min, and suitable ranges may be selected from between any of these values. The timing of mixing may depend on assay requirements such as sample volume, viscosity, composition and detection ranges of target analyte.

To effect mixing, the magnets (e.g. electromagnets) may be arranged at substantially opposed end of a channel, or of the microfluidic device 1. For example, magnets may be controlled or switched such that they pull the magnetisable particles towards one end of a channel or the microfluidic device 1, and then the effect reversed to pull the magnetisable particles towards another end of the channel or the microfluidic device 1. This cycle may be repeated multiple times until the desired level of mixing has been achieved.

The magnets may be electromagnets. The electromagnets may exert a field strength of about 0.5, 1, 5, 10, 15, 20, 25, 30, 35, 40, 45 or 50 Gauss, and suitable ranges may be selected from between any of these values.

When the sample is ready for analysis, the magnets may then be controlled or switched to position the magnetisable particles into close proximity to the magnetic sensors. The magnets may exert a magnet field strength of about 0.01, 0.05, 0.1, 0.2, 0.3, 0.4, 0.5, 0.6, 0.7, 0.8, 0.9, 1, 5, 10, 50 or 100 Gauss, and suitable ranges may be selected from between any of these values. The sample data is then acquired as described.

The magnetisable particles are sensed by a magnetic sensor.

The magnetic sensor may be selected from spintronic sensors, atomic magnetometers (AMs), nuclear magnetic resonance (NMR) systems, fluxgate sensors, Faraday induction coil sensors, diamond magnetometers, and domain walls-based sensors.

The volumetric-based sensors, such as planar hall effect (PHE) sensors provide simple and rapid sample preparation and detection. Surface-based sensors, such as giant magnetoresistance (GMR) offer a lower detection limit (single particle) due to the short distance between the magnetisable particles and the sensor. However, these techniques typically require laborious sample and/or substrate preparation. Optimising magnetisable particles for specific applications and selecting appropriate detection methods remain challenging for the magnetic nanotechnology community due to the increasing demands of detection sensitivity, molecular specificity, and application complexity. The spintronic sensors may be selected from giant magnetoresistance (GMR), tunnel magnetoresistance (TMR), anisotropic magnetoresistance (AMR), and planar Hall effect (PHE) sensors.

The GMR effect was discovered in the 1980s and has traditionally been used in data recording. The spin valve provides higher sensitivity with a micron-sized design. A spin-valve GMR sensor consists of an artificial magnetic structure with alternating ferromagnetic and nonmagnetic layers. The magneto resistance effect is caused by the spin-orbital coupling between conduction electrons crossing the different layers. The variation in magnetoresistance provides quantitative analysis by this spin-dependent sensor. GMR sensors may be used to detect DNA-DNA or protein (antibody)-DNA interactions. The dimensions of the sensor array may be adjusted for the detection of individual magnetisable particles. GMR sensors may be used in combination with antiferromagnetic particles.

The planar Hall effect is an exchange-biased permalloy planar sensor based on the anisotropic magnetoresistance effect of ferromagnetic materials. The PHE sensor may be a spin-valve PHE or PHE bridge sensor. The PHE sensor may be able to carry out single-particle sensing.

Described is a method for detecting analytes in a sample comprising:

bringing a sample comprising a target analyte into contact with magnetisable particles, the particles being coated with binding molecules complementary to the target analyte resulting in bound and unbound binder complexes, positioning the magnetisable particles, comprising both bound and unbound binder complexes, in proximity to a magnetic field sensor, changing the magnetic field sufficient to release at least a portion of the magnetisable particles, comprising both bound and unbound binder complexes, from their proximity to the magnetic field sensor, and measuring changes in a magnetic signal detected from the net movement (i.e. translational or rotational movement) of magnetisable particles relative to the magnetic sensor.

As shown in FIG. 1, a set up according to an embodiment of this method may broadly comprise a microfluidic device, a sensor, a magnet, a signal amplifier, an analog to digital converter and a computer.

The target analyte can be any substance or molecule that is complementary to and capable of being bound by a binding molecules provided to the magnetisable particles. For example, the target analyte can be selected from the group comprising of a protein, a peptide, a nucleic acid, lipid or a carbohydrate.

The target analyte may be a protein or a fragment thereof selected from the group comprising of an antibody, an enzyme, a signalling molecule or a hormone.

The target analyte may be a nucleic acid selected from the group comprising of DNA, RNA, cDNA, mRNA, or rRNA.

The method may detect more than one target analyte in a single sample. For example, the method may detect two or more, three or more, four or more, five or more, 10 or more, 15 or more, 20 or more target analytes in a single sample.

The sample to be analysed can be any sample that may contain one or more target analyte(s). For example, the sample may be a clinical, veterinary, environmental, food, forensic or other suitable biological samples.

The clinical sample may be selected from a bodily fluid. For example, the bodily fluid may be selected from blood, sweat, saliva, urine, sputum, semen, mucous, tears, cerebral spinal fluid, amniotic, gastric juices, gingival crevicular or interstitial fluids.

The environmental sample may be selected from the group comprising of water, soil or an aerosol.

A benefit of the present invention may be that the sample preparations are not laborious or difficult to prepare. The sample preparation utilises established biochemistries for molecular functionalisation and attachment, either on microfluidic surfaces or magnetisable particle surfaces.

The sample to be analysed may be added directly to a sample well or microfluidic device without additional processing.

The sample may be subjected to one or more sample processing steps. It will be understood that suitable sample processing steps may depend on the type and/or nature of the sample to be analysed. In some embodiments, sample processing steps may be selected from the group comprising dilution, filtration, or extraction (e.g. liquid-liquid, solid-phase). For example, whole blood samples may be filtered using cellulose based filters to isolate plasma to be analysed.

A first step of the method may comprise combining the sample to be analysed with a preparation containing freely diffusible magnetisable particles that are coated with binding molecules (the binder complex) complementary to the target analyte in a sample well or sample reservoir. Where appropriate, the term 'binder complex' may be used interchangeably to refer to the magnetisable particles that are coated binding molecules.

In some embodiments the magnetisable particles may have limited diffusibility. This may occur where the magnetisable particles are cross-linked or derivatised with macromolecules.

The macromolecules may be a hydrogel or PEG linker. This may occur when using the device for multiplexing assays for detection of multiple targets or samples in the one sample.

The present method may improve the rate at which the binding molecules bind target analytes by providing binder complexes that are mobile and freely diffusible in solution. When the sample and binder complex preparation are combined, the binder complexes are freely diffusible and the binding molecules are able to interact with the target analytes throughout the entire sample volume. As both the binder complex and target analytes are freely diffusible and suspended in the sample volume, the average physical distance between a target analyte and a binder complex is likely to be small. As such, the rate of binding may be improved and binding equilibrium may be achieved significantly faster.

In detection assays such as ELISA, binding molecules such as antibodies are immobilised on macro scale objects such as the surface of a test well. In such a method, the physical distance between a target analyte and an antibody may vary significantly depending on the position of the analyte in the sample volume. For example, a target analyte near the top of the sample volume may be quite far from the immobilised antibody and will be less likely to be captured and bound. As such, the rate of binding may be limited by the rate at which target analytes diffuses in the sample volume towards the immobilised antibodies.

The sample and binder complex may be allowed to combine for a suitable amount of time to enable binding molecules to reach binding equilibrium. In some embodiments, the suitable amount of time to enable binding to reach equilibrium may be about one, two, three, four, five, 10, 20, 30, 45, 60, 90, 120, 180, 240, 300 or 360 second(s) and useful ranges may be selected between any of these values, (for example from about 1 to 30, 1 to 60, 1 to 120, 10 to 30, 10 to 60, 10 to 90, 30 to 60, 30 to 90, 30 to 120, 60 to 90, 60 to 120, 60 to 180, 90 to 120, 90 to 180, 90 to 240, 180 to 240, 180 to 300, 180 to 360 seconds).

The magnetic field generator may be used to induce magneto-hydrodynamic mixing of the sample to improve the rate at which binding equilibrium is reached. In such an embodiment, the magnetic field generator is used to induce movement of the binder complexes in the sample volume.

A signal to allow quantification of the analyte in the sample is generated by measuring the change in magnetic field as the bound analyte moves away from the magnetic field sensor.

The magnetic field sensor may be an on-chip magnetometer. The magnetic field sensor may have a sensitivity of at least 1 mV/V/gauss. In some embodiments, the magnetic field sensor may detect and/or measure a magnetic field of at least about 10 mGauss, 1 mGauss, 100 μGauss, or 10 μGauss.

The magnetic field sensor may comprise multiple axis, for example one, two or three-axis.

The magnetic field sensor may be a Honeywell HMC 1021S magnetometer. In another embodiment, the magnetic field sensor may be a Honeywell HMC1041Z magnetic sensor. In other embodiments, the magnetic field sensor may be selected from the group comprising Honeywell HMC 1001, HMC 1002, HMC 1022, HMC 1051, HMC 1052, HMC 1053, or HMC 2003 magnetometers.

The magnetic field sensor may comprise a bespoke magnetic field sensor having custom components.

Multiple magnetic field sensors may be used simultaneously to measure the change in magnetic field. For example, two, three, four, five, six, seven, eight, nine, 10, 12, 14, 16, 18, 20, 22, or 24 magnetic field sensors for small portable applications.

The magnetic field sensors may be provided in a relatively small area in the device. For example, 24 magnetic field sensors may be provided to an area of about 13 mm×19 mm. Such a configuration enables faster sample-to-data times, as discussed above, due the shorter microfludic channels that are used with this magnetic field sensor configuration. This configuration further enables a smaller and more portable device.

The device may comprise about 5, 6, 7, 8, 9, 10, 11, 12, 13, 14, or 15 magnetic field sensors per cm$^2$ of the printed circuit board, and useful ranges may be selected between any of these values, (for example, about 5 to about 15, about 5 to about 13, about 5 to about 10, about 6 to about 15, about 6 to about 12, about 6 to about 9, about 7 to about 15, about 7 to about 14, about 7 to about 13, about 7 to about 10, about 8 to about 15, about 8 to about 14, about 8 to about 11, about 9 to about 15, about 9 to about 13 or about 10 to about 15 sensors per cm$^2$ of the printed circuit board).

In some embodiments, multiple magnetic field sensors may be used simultaneously to measure the change in magnetic field. For example, 50, 60, 70, 80, 90, 100, 110 or 120 magnetic field sensors for small portable applications and in situ laboratory or clinical applications, and useful ranges may be selected between any of these values, (for example about 50 to about 120, about 50 to about 100, about 50 to about 90, about 50 to about 80, about 60 to about 120, about 60 to about 110, about 60 to about 90, about 70 to about 110, about 70 to about 90, about 80 to about 120 or about 80 to about 110 magnetic field sensors).

In some embodiments, multiple magnetic field sensors may be used simultaneously to measure the change in magnetic field. For example, 1000, 1250, 1500, 1750, 2000, 2250, 2500, 2750 or 3000 magnetic field sensors for laboratory or clinical, research or industrial applications.

A further step of the present method may comprise applying a magnetic field to the sample to position binder complexes in proximity to the magnetic field sensor. A magnetic field generator as described above may be used to generate a magnetic field to manipulate bound and unbound binder complexes into a position that enables the magnetic field sensor to effectively measure the changes in magnetic field generated by the magnetisable particles.

In some embodiments, the binder complexes may be positioned in proximity to the magnetic field sensor using microfluidics, acoustics, piezoelectricity or other suitable means. In other embodiments, the binder complexes may be positioned by centrifugation.

In some embodiments, the magnetic field may be generated in a direction that moves the magnetisable particles in the sample volume towards the magnetic field sensor. The magnetic field sensor may be provided in any position relative to the test well or microfludic device. For example, if the magnetic field sensor is positioned below a test well or sample reservoir, the magnetic field will move the magnetisable particles towards the bottom of the test well or sample reservoir. In another example, if the magnetic field sensor is positioned above a test well or sample reservoir, the magnetic field will move the magnetisable particles towards the top of the test well or sample reservoir.

In some embodiments, the magnetic field generated may be static or dynamic.

In some embodiments, the strength of the magnetic field generated may be modulated.

Without wishing to be bound by theory, the modulation of this magnetic field (i.e. the bias field) has the primary function of aligning the magnetisable particles to the sensor to achieve the highest sensitivity of detection during detection. For ferromagnetic particles, given they have their own permanent magnetic field, where the bias field is switched off resulting in misalignment of the magnetic particles. For paramagnetic (or superparamagnetic) particles, as their magnetic field has to be induced by an external field, the bias field serves the additional function of inducing such a field.

The bias field may be modulated in order to support different magnetisable particles since different particles (whether by chemical composition or physical size) may require different bias field strengths and configurations.

In some embodiments, the magnetic field may be generated and positioned in such a way as to maximise its effect on the magnetisable particles but minimise its effect on the magnetic field sensor. The magnetic field generator may be generated and/or positioned in close proximity to the magnetic field sensor. In some embodiments, the magnetic field generator is positioned above, below or beside the magnetic field sensor. In some embodiments, the magnetic field generator may be positioned on the same plane vertical or horizontal plane as the magnetic field sensor.

A further step of the method may comprise changing the magnetic field sufficiently to release at least a portion of the binder complexes from their proximity to the magnetic field sensor when the bound and unbound binder complexes are positioned in proximity to the magnetic field sensor.

In some embodiments, the magnetic field may be reduced gradually.

In some embodiments, the magnetic field may be removed instantly.

In some embodiments, the magnetic field may be variable in shape.

As the magnetic field applied to the sample is reduced and/or removed, the bound and unbound binder complexes are released from the magnetic field and may freely diffuse away (translational movement) from their proximity to the magnetic field sensor. The binder complex may also rotate relative to the magnetic field sensor (rotational movement) as the magnetic field applied to the sample is reduced and/or removed.

According to the present method, bound and unbound binder complexes may be distinguished based on the change in molecular diffusion characteristics according to Graham's law of molecular diffusion which states that the rate of diffusion is inversely proportional to the square root of its molecular weight. The rate of diffusion may be calculated using the formula below:

$$\frac{R_A}{R_B} = \sqrt{\frac{M_B}{M_A}}$$

where
$R_A$=the rate of diffusion for molecule A,
$R_B$=the rate of diffusion for molecule B,
$M_A$=the molecular weight of molecule A, and
$M_B$=the molecular weight of molecule B.

As a binder complex that is bound to a target analyte will have larger molecular weight compared to an unbound binder complex, the unbound binder complex will have a higher rate of diffusion according to Graham's law. Therefore, bound and unbound binder complexes may be distinguished based on their kinetic profiles.

A further step of the present method may comprise measuring the changes in a magnetic signal detected from the magnetisable particles as they move (via translational or rotational movement) in relation to the magnetic field sensor. The magnetic field sensor, as described in detail the preceding paragraphs, measures the changes in the magnetic field strength generated by the magnetisable particles over time. The present method uses magnetic field changes over time which only requires one binding molecule for binding of the target analytes.

In some embodiment, magnetic field changes over time may be determined by measuring magnetoresistance effect and the signal drop-off over time.

The magnetic field signal generated by the magnetisable particles in relation to the magnetic field sensor conforms to the magnetic dipole field equation:

$$B(m, r) = \frac{\mu_0}{4\pi} \frac{3(m \cdot \hat{r})\hat{r} - m}{r^3}$$

where

B is the field r is the vector from the position of the dipole to the position where the field is being measured r is the absolute value of r: the distance from the dipole $\hat{r}=r/r$ is the unit vector parallel to r:

m is the (vector) dipole moment $\mu_0$ is the permeability of free space

Based on the magnetic dipole field equation, the detection signal drops off to the distance cubed from the magnetic field sensor. This phenomenon in conjunction with the diffusion kinetics described above can be used for signal generation described in the proceeding paragraphs.

Due to the higher diffusion rate of unbound binder complexes, the unbound binder complexes may move further away from the sensor at a faster rate when compared to binder complexes that are bound to target analytes. The difference in diffusion rate will generate a magnetic field decay signal over time. The rate of decay is dependent on the molecular weight of the bound and unbound binder complexes where an unbound binder complex will have a faster rate of decay compared to a bound binder complex.

The rate of decay may be modelled in a decay curve. The decay curve may be used to distinguish between bound and unbound binder complexes. For example, an accelerated decay curve may indicate unbound binder complexes and an attenuated decay curve may indicate bound binder complexes.

The method may comprise multiple rounds of the following steps to generate a signal curve over time to distinguish bound and unbound binder complexes to quantify the target analyte.

Applying a magnetic field to position the magnetisable particles in proximity to a magnetic field sensor.

Changing the magnetic field sufficient to release at least a portion of the magnetisable particles from their proximity to the magnetic field sensor.

Measuring changes in a magnetic signal detected from the magnetisable particles as the magnetisable particles move away from the magnetic sensor.

The method may comprise a reference calibration step by measuring the total magnetic field strength generated by the bound or unbound binder complexes.

The magnetic field signal generated by the magnetisable particles may be due to the inherent properties of the magnetisable particles or it may be induced by an external magnetic field.

The magnetic field sensor is positioned in such a way as to maximise its sensing of the magnetisable particles but minimise sensing of the magnetic field generator.

The magnetic field or signal from the magnetisable particles can be inherent to its atomic construct, or can be induced by an external magnetic field.

Data acquisition by the sensor may be synchronised with the microfluidic device. This may allow data from the detected sensor to be characterised between sample data or environmental or ambient data. For example, detection by the magnetic sensor of a signal absent sample injection into the microfluidic device would characterise that data as environmental or ambient data. Characterisation of the data as environmental or ambient data may assist to establish background and may also assist preparing calibration data.

Where the magnetic sensor detects a signal following injection of the sample into a microfluidic device, which coincides with the positioning of the magnetisable particles into close proximity with the magnetic sensor, such data can be characterised as sample data.

Data acquisition from the sensor may be continuous. That is, the magnetic sensor continuously transmit signals and, based on the synchronisation of the data collection with the injection of sample into the microfluidics device, characterises the data as sample data or background data.

The sensor data may be acquired over a period of time in order to measure changes in the magnetic signal from the magnetisable particles. Actions or events may be inferred from changes in the sensed magnetic signal. The actions or events include may include movement of the magnetisable particles from fluid flow, from external magnetic forces, or from diffusion.

The method may comprise processing the raw data output from the magnetic field sensor to quantify the amount of target analyte in the sample. Raw data processing may be carried out using a combination of hardware and software implementations described in detail in the preceding paragraphs.

The processing of the raw data output may comprise amplifying the signal output from the magnetic field sensor using a signal amplifier. The signal output from the magnetic field sensor may be a voltage reading that is proportional to the sensed magnetic field. In some embodiments, the signal amplifier is a Texas Instruments INA819 amplifier.

The voltage reading from the magnetic field sensor may be amplified in magnitude to a higher voltage (in proportion to the original voltage reading) that is compatible with data processing and collection electronic components.

The processing of the raw data output may further comprise converting the analog data output from the magnetic field sensor into a digital data output. For example, the voltage reading may be converted into digital bitstream that is recordable by a computer.

Analog to digital conversion may be performed using an analog to digital converter (ADC).

The conversion or sampling resolution may be 16, 24, 32, 64, 128, 256, or 512 bit.

An evaluation of the analytical performance of a detection methodology is often done by measuring dose-response curves from which the limit of detection (LoD) can be derived. The LoD is the lowest quantity of a substance such as a biomarker that can be detected for a chosen confidence level. The chosen assay (biomarker, biomaterials, sample matrix, incubation times, etc.) may have a strong influence on the LoD. Also used is the limit of quantification (LoQ) that is the lowest biomarker concentration that can be quantified with a given required precision. The LoQ is close to the LoD if a dose-response curve has a good sensitivity, i.e. if the signal changes strongly as a function of the target concentration.

The present method may provide for an LoQ of about 0.05, 0.1, 0.2, 0.3, 0.4, 0.5, 0.6, 0.7, 0.8, 0.9, 1.0, 1.5 or 2.0 pg/mL, and suitable ranges may be selected from between any of these values.

The present method may provide for an LoD of about 0.1, 1.1, 1.2, 1.3, 1.4, 1.5, 1.6, 1.7, 1.8, 1.9 or 2.0 pg/mL, and suitable ranges may be selected from between any of these values.

The invention describes methods, reagents and systems that detect and quantitate analytes in a sample.

High-throughput screening (HTS) systems enable a large number of assays to be conducted in a relatively short time. HTS systems may comprise microplates, microplate readers, robotic liquid and microplate handling platforms. In some embodiments, one or more steps of the presently described method may be carried out using HTS systems.

In some embodiments, the microplates may comprise, for example, 6, 12, 24, 48, 96, 384 or 1536 sample wells.

In some embodiments, the magnetic sensor(s) may be provided to the microplates.

In some embodiments, robotic liquid handling devices may be used to distribute samples and/or reagents on the microplates.

In some embodiments, the present method may be partially or fully automated using HTS systems.

The device for detecting an analyte may be operable in any orientation. The operation of the device or performance of the present method is not dependent on gravity to function effectively. That is, the device can perform the present method regardless of how the device is orientated. For example, the device may be operable in an inverted configuration where the magnetic field sensor is orientated above the sample reservoir or microfluidic device.

It will be appreciated that the present method may broadly be used in any application requiring detection and/or quantification of a target analyte. In particular, the method may be used in applications requiring i) rapid determination, or ii) sensitive determination, or iii) quantitative determination, or iv) or any combination of (i) to (iii);

of the presence of target analytes in samples.

For example, suitable applications may include clinical, veterinary, environmental, food safety or forensic applications.

In some embodiments, the clinical application may include diagnostic detection of biomarkers in a sample that may be indicative of a clinical condition. In one example, the method may be used for rapid, sensitive, and quantitative diagnostic detection of specific antibodies in a blood sample which may indicate potential infection by a pathogen. In a further example, the method may be used for diagnostic detection of specific protein biomarkers that are overexpressed in cancers. The diagnostic detection may be performed on samples across different species.

The clinical condition may be selected from infections, such as infections from bacteria, fungi, viruses (e.g. hepatitis and HIV) (e.g. biomarkers such as hepatitis and HIV antibodies), parasites (e.g. microbial parasites [e.g. malarial], nematodes, insect parasite).

The clinical condition may be selected from diseases such as cardiac disease (biomarkers such as BNP), cancer (e.g. solid organ cancers, blood cancers, other cancers), (e.g. biomarkers such as Ca-125 and other tumour markers), neurological diseases (e.g. multiple sclerosis, Alzheimer's disease, Parkinson's disease, Huntington's disease) (e.g. biomarkers such as CNS immunoglobulins), respiratory diseases (e.g. biomarkers such as serum ACE), liver disease (e.g. biomarkers such as liver function tests and albumin), kidney disease (e.g. biomarkers such as creatinine and protein).

The clinical condition may be selected from organ injury or failure such as brain injury (e.g. biomarkers such as Glial fibrillary acidic protein or GFAP), kidney injury (e.g. biomarkers such as serum creatine), heart damage (e.g. biomarker such as creatine kinase-muscle), lung damage (e.g. biomarkers such as intercellular adhesion molecule-1 or ICAM1), or liver injury (e.g. biomarker such as alkaline phosphatase).

The clinical condition may be selected from endocrine disorders such as diabetes (e.g. biomarkers such as insulin, elevated, HbA1C, thyroid dysfunction, thyroid hormone, pituitary disorders (e.g. biomarkers such as ACTH, prolactin, gonadotrophins, thyroid stimulating hormone, growth hormone, antidiuretic hormone), parathyroid disorders (e.g. biomarkers such as, parathyroid hormone), adrenal disorder (e.g. biomarkers such as cortisol, aldosterone, adrenaline, DHEAS), sex hormone imbalance (e.g. biomarkers such as androgens and estrogens), carcinoid tumour (e.g. biomarkers such as 5-HIAA, VIPoma, serum VIP), elevated bone turnover (e.g. biomarkers such as P1NP).

The clinical condition may be selected from lipid disorders (e.g. biomarkers such as cholesterols and triglycerides)

The clinical condition may be selected from nutritional disorders (e.g. vitamin deficiencies, malabsorption syndrome, malnutrition, disorders of vitamin metabolism), (e.g. biomarkers such as vitamin levels, iron levels, mineral levels).

The clinical condition may be selected from inflammation or inflammatory disorders (e.g. biomarkers such as ESR, Crp and other acute phase proteins).

The clinical condition may be selected from autoimmune diseases (e.g. biomarkers such as specific antibody markers).

The clinical condition may be selected from allergic disease (e.g. biomarkers such as tryptase).

The clinical condition may be selected from physical trauma such as electrocution (e.g. biomarkers such as creatinine kinase).

The clinical condition may be selected from immune deficiency disorders (e.g. common variable immune deficiency), (e.g. biomarkers such as complement, leucocytes and immunoglobulins).

The clinical condition may be selected from clotting disorders (e.g. thrombophilia)(e.g. biomarkers such as biomarkers such as clotting factors and other markers).

The clinical condition may be selected from inherited or acquired enzyme disorders, deficiency or excess and other congenital or acquired defects of metabolism (e.g. Bartter syndrome, congenital adrenal hyperplasia), (e.g. biomarkers such as electrolytes, enzyme levels, metabolic products of enzymes).

The clinical condition may be selected from electrolyte disturbance such as hyperkalaemia and hypernatraemia (e.g. biomarkers such as electrolytes).

The clinical condition may be selected from drug adverse effects or poisoning (eg. biomarkers such as drug levels and levels of drug metabolites.

Specific to veterinary medicine, the clinical condition may be selected from renal failure, FIV/AIDS (Feline), cancers, and any biomarker for organ function/failure.

In some embodiments, the clinical conditions may be conditions in veterinary subjects such as feline, canine, bovine, ovine, equine, porcine, or murine.

In some embodiments, the environmental application may include detection of pollutants in an environmental sample. The environmental pollutant may be selected from such pollutants as, for example, lead, particulate matter, micro plastic and hormones.

For example, the method may be used for monitoring and quantifying heavy metals in a water sample.

In some embodiments, the food safety application may include detection of pathogen in food samples. For example, the method may be used to rapidly and sensitively detect post-pasteurisation contamination in milk by bacterial pathogens.

EXAMPLES

Example 1: Sensitivity and Limit of Detection

The purpose of this study was to test the sensitivity of detection.

Specific amounts of magnetisable particles were added to the microfluidics system for detection. The setup of the system is summarised below.

Magnetic sensor: Honeywell HMC 1021S magnetometer

Magnetisable particles: Thermo Fisher Dynaparticles T1 (1 μm) Streptavidin particles Biolabel: Streptavidin Amplifier: Texas Instrument INA826

Number of particles:

Sample 1: control—0 pg of particles

Sample 2: 0.5 pg of particles

Sample 3: 5 pg of particles

Sample 4: 50 pg of particles

Sample 5: 500 pg of particles

Sample 6: 50,000 pg of particles

Sample 7: 500,000 pg of particles

Acquisition of sensor data:

0.012 seconds per read 1,200 reads per sample approximately 15 seconds total read time After being introduced into the microfluidics system the particles were positioned over the sensor by the microfluidics device. The magnet was activated to bring the magnetisable particles into close proximity to the magnetic sensor. The magnet was then turned off and a permanent magnet positioned underneath the sensor was used to generate a bias field. The magnetic field sensor measured changes in the magnetic field strength generated by the magnetisable particles over time as they diffused away from the magnetic sensor. The device determines the amount of analyte in the sample by measuring the net movement of the magnetisable particles relative to the magnetic field sensor.

Sensor data was acquired for each sample.

The sensor data was then processed as follows. A 30 sample window moving average filter was applied and the data was averaged across time and normalised to the negative control sample (sample 1).

Figure 3:
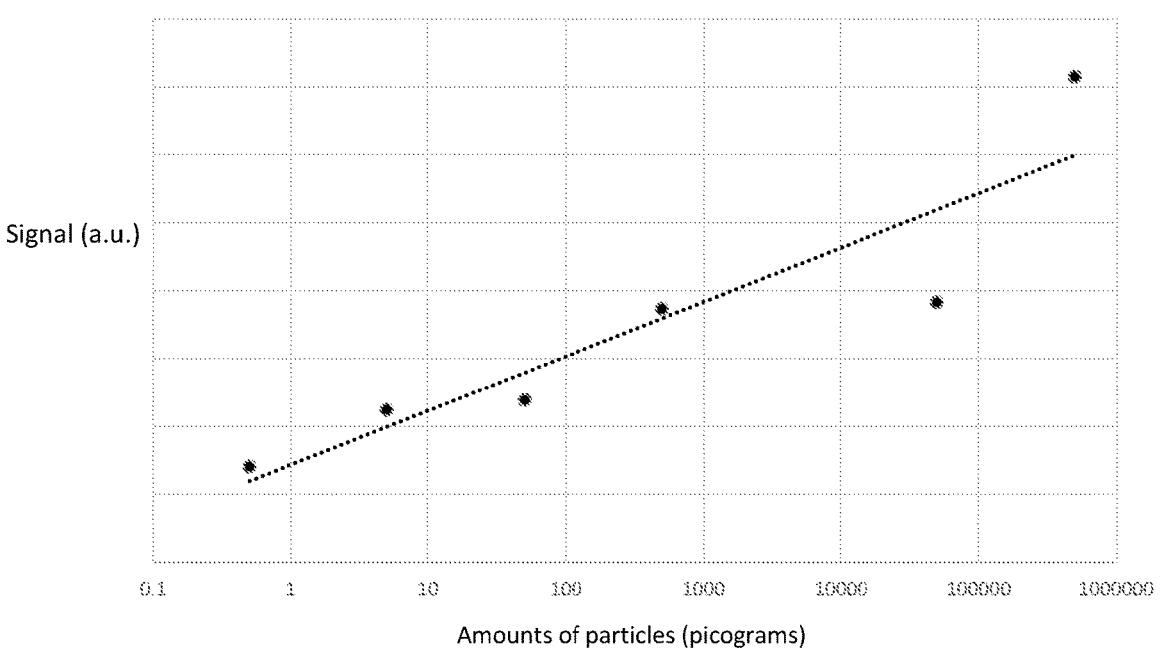
FIG. 3 is a graph showing a signal vs sensitivity plot showing an LoQ of about 0.5 pg.

FIG. 3 is a graph showing the signal detected with the vertical axis expressed as the signal as arbitrary units (a.u.).

The amount of particles are expressed as picograms (pg) on the horizontal axis.

The results demonstrate that the sensitivity and signal acquisition is improved with a greater number of particles.

The graph of FIG. 3 is a sensitivity plot and demonstrates an LoQ of about 0.5 pg.

Example 2: Speed of Detection

The purpose of this study was to test the speed of detection system.

Specific amounts of magnetisable particles were added to the microfluidics system for detection. The setup of the system is summarised below.

Magnetic sensor: Honeywell HMC 1021S magnetometer

Magnetisable particles: Thermo Fisher Dynaparticles T1 (1 μm) Streptavidin particles Biolabel: Streptavidin Amplifier: Texas Instrument INA826

Number of particles:

Sample 1: control—0 pg of particles

Sample 2: 50 pg of particles

Sample 3: 500,000 pg of particles

Acquisition of sensor data:

0.012 seconds per read 1,200 reads per sample approximately 15 seconds total read time After being introduced into the microfluidics system the particles were positioned over the sensor by the microfluidics device. The magnet was activated to bring the magnetisable particles into close proximity to the magnetic sensor. The magnet was then turned off and a permanent magnet positioned underneath the sensor was used to generate a bias field. The magnetic field sensor measured changes in the magnetic field strength generated by the magnetisable particles over time as they diffused away from the magnetic sensor. The device determines the amount of analyte in the sample by measuring the net movement of the magnetisable particles relative to the magnetic field sensor.

Sensor data was acquired for each sample.

The sensor data was then processed as follows. A 30 sample window moving average filter was applied and the data normalised to the negative control sample (Sample 1).

Figure 4:
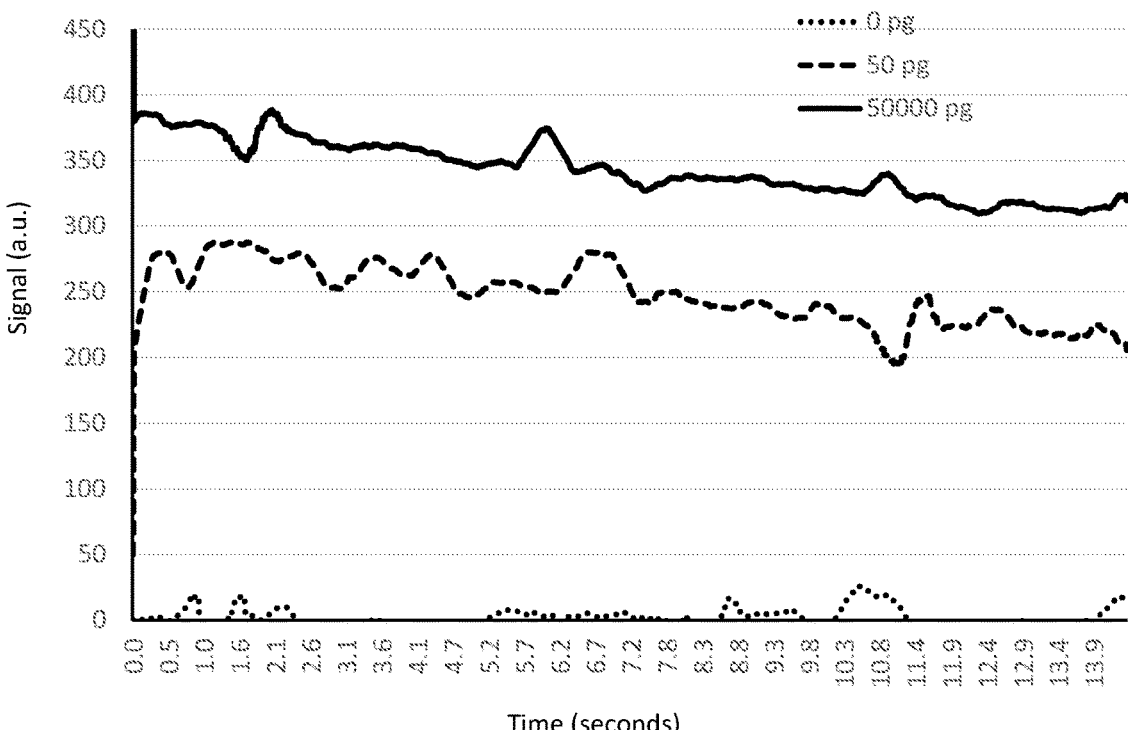
FIG. 4 is a graph showing signal acquisition over time for control, 50 pg of particles and 500,000 pg of particles.

Shown in FIG. 4 is a graph showing the signal acquisition over time with the vertical axis expressed as the signal as arbitrary units (a.u.).

Time point for each read expressed as seconds (s) on the horizontal axis.

The results demonstrate that the method can acquire sufficient signal within 15 seconds to qualitative measure and discriminate the amount of particles presented within the sample.

The graph of FIG. 4 is a time for data acquisition plot and demonstrates fast sample detection and data collection in under 15 seconds.

The graph of FIG. 4 shows that the above system is responsive to very low amounts of particles (i.e. in the picogram range) and can detect and discriminate rapidly in seconds.

Example 3: Detection of Streptavidin Protein in a Sample

The purpose of this study was to demonstrate quantitative detection of streptavidin protein in a sample as a target analyte.

Biotin conjugated to latex-particles (non-magnetisable particles) were used to capture and associate with specific amounts of streptavidin added to the microfluidics system for detection. The setup of the system is summarised below.

Magnetic sensor: Honeywell HMC 1021S magnetometer

Magnetisable particles: Thermo Fisher Dynaparticles T1 (1 um) Streptavidin particles Biolabel: Streptavidin Amplifier: Texas Instrument INA826

Samples

Sample 1: 0 pmoles/ml streptavidin protein conjugated to the magnetisable particles Sample 2: 0.33 pmoles/ml streptavidin protein conjugated to the magnetisable particles Sample 3: 3.3 pmoles/ml streptavidin protein conjugated to the magnetisable particles Sample 4: 33 pmoles/ml streptavidin protein conjugated to the magnetisable particles Sample 5: 330 pmoles/ml streptavidin protein conjugated to the magnetisable particles Acquisition of sensor data:

0.012 seconds per read 1,200 reads per sample approximately 15 seconds total read time After being introduced into the microfluidics system the particles were positioned over the sensor by the microfluidics device. The magnet was activated to bring the magnetisable particles into close proximity to the magnetic sensor. The magnet was then turned off and a permanent magnet positioned underneath the sensor was used to generate a bias field. The magnetic field sensor measured changes in the magnetic field strength generated by the magnetisable particles over time as they diffused away from the magnetic sensor. The device determines the amount of analyte in the sample by measuring the net movement of the magnetisable particles relative to the magnetic field sensor.

Sensor data was acquired for each sample.

The sensor data was then processed as follows. A 30 sample window moving average filter was applied and the data was averaged across time and normalised to the negative control sample (sample 1).

Shown in Table 1 is the signal detected via biotin-capture and association of Streptavidin protein the signal as arbitrary units (a.u.).

TABLE 1

Concentration of Streptavidin vs detection signal

| Concentration of Streptavidin | | Detection Signal |
|---|---|---|
| (pmol/mL) | (ng/mL) | (a.u.) |
| 0.00 | 0.00 | 0.00 |
| 0.33 | 17.5 | 163.74 |
| 3.30 | 175 | 198.26 |
| 33.00 | 1750 | 224.43 |
| 330.00 | 17500 | 480.68 |

Table 1 demonstrates that the method of the current invention can detect levels of streptavidin at 3.3 pmol/mL and lower.

Example 4: Sensitivity and Limit of Quantification

The purpose of this study is to demonstrate sensitivity and quantitative detection of biomarkers in samples from different species.

Magnetisable particles were functionalised with recombinant antibodies, with each antibody targeting a specific biomarker respectively. The functionalised magnetisable particles were used to capture and associate with specific concentrations of biomarkers in each sample added to the microfluidics system for quantification. The setup of the system is summarised below.

Magnetic sensor: Honeywell HMC 2003 magnetometer

Magnetisable particles: Nanocs MP25-AV (30 nm diameter) chemically functionalised with antibodies:

Anti-human CRP detection antibody (R&D systems DY1707)

Anti-human albumin detection antibody (R&D Systems DY1455)

Anti-canine IL-6 detection antibody (R&D Systems DY1609)

Anti-canine VEGF-A detection antibody (R&D Systems DY1603)

Anti-feline TNFa detection antibody (R&D Systems DY2586)

Anti-feline GM-CSF detection antibody (R&D Systems DY987)

Anti-equine TNFa detection antibody (R&D Systems DY1814)

Amplifier: Honeywell HMC 2003 in-built amplifier

Acquisition of sensor data:

0.007 seconds per read 1,000 reads per sample approximately 10 seconds total read time Samples (recombinant protein):

Human CRP

Human Albumin

Canine IL-6

Canine VEGF-A

Feline TNFa

Feline GM-CSF

Equine TNFa

After being introduced into the microfluidics system the particles were positioned over the sensor by the microfluidics device. The magnet was activated to bring the magnetisable particles into close proximity to the magnetic sensor (the 'capture' step). The magnet was then turned off (the 'release' step). The magnetic field sensor measured changes in the magnetic field strength generated by the magnetisable particles over time as they diffused away from the magnetic sensor.

Sensor data was acquired for each sample.

The sensor data was then processed as follows. The data was averaged across the first 10 reads then normalised for each relative negative control sample.

Shown in Table 2 are the sensor values (arbitrary units [a.u.]) detected via antibody capture and association with biomarkers for each sample.

TABLE 2

Concentration of biomarkers vs sensor value

| Concentration of biomarker (pg/ml) | Sensor value (a.u.) | | | | | | |
|---|---|---|---|---|---|---|---|
| | Human CRP | Human Albumin | Canine IL-6 | Canine VEGF-A | Feline TNFa | Feline GM-CSF | Equine TNFa |
| 10000 | 0.033 | 0.057 | 0.020 | 0.031 | — | 0.031 | 0.028 |
| 1000 | 0.031 | 0.042 | 0.019 | 0.026 | 0.026 | 0.035 | 0.025 |
| 100 | 0.030 | 0.033 | 0.011 | 0.026 | 0.018 | 0.031 | 0.026 |
| 10 | 0.010 | 0.023 | 0.016 | 0.019 | 0.013 | 0.019 | 0.017 |
| 1 | 0.010 | 0.032 | 0.008 | 0.010 | 0.012 | 0.012 | 0.015 |
| 0.1 | — | 0.008 | — | 0.007 | 0.009 | 0.011 | 0.008 |
| 0 | 0 | 0 | 0 | 0 | 0 | 0 | 0 |
| R2 value | 0.88 | 0.86 | 0.88 | 0.95 | 0.91 | 0.90 | 0.96 |

The results in Table 2 demonstrate a limit of quantification in the 0.1 pg/mL range across a range of biomarkers from various species. The results also demonstrate biomarker detection across 6-orders of magnitude from 0.1 to 10,000 pg/mL.

We claim:

1. A device for detecting an analyte in a sample, comprising a passive microfluidic device comprising a sample insertion area, a non-sample well zone, and a sample well zone located therebetween, the sample well zone comprising sample wells, and channels that juncture at the sample wells, the non-sample well zone having the channels and absent any sample wells, one or more magnets adapted to generate a magnetic field in the sample well, and a magnetic field sensor located at the sample well for measuring changes over time in the magnetic field proximate the sample well, and wherein the one or more magnets are adapted to control a position of magnetisable particles relative to the magnetic field sensor and the magnetic field sensor is adapted for use such that the magnetic field sensor can detect a change in the magnetic field based on the net movement of the magnetisable particles in relation to the magnetic field sensor, and wherein at least one of the sample wells junctures with three or more of the channels to increase flow of the sample towards the magnetic field sensor located at the sample well.

2. The device of claim 1, wherein the magnetisable particles are functionalised with molecules that specifically bind to the analyte.

3. The device of claim 1, wherein the magnetisable particles are ferro-magnetic or paramagnetic.

4. The device of claim 1, wherein the device is configured to carry out signal multiplexing using a multiplex chipset configured to perform simultaneous detection of multiple analytes in the sample.

5. The device of claim 1, wherein the magnetisable particles have an average particle size of about 5 to 5000 nm.

6. The device of claim 1, wherein the sensor is adapted to continuously acquire the signal data from the magnetic field sensor.

7. The device of claim 1, wherein the channels have a cross section of about 0.001 $mm^2$ to 1 $mm^2$.

8. The device of claim 1, further comprising a printed circuit board having 5 to 15 magnetic fields sensors per cm2 of the printed circuit board.

9. The device of claim 1, wherein the device is operable in any orientation.

10. The device of claim 1, wherein the sample wells junction with two or more channels.

11. The device of claim 1, wherein the one or more magnets are adapted to exert a magnetic field strength of about 0.01 to about 100 Gauss at the sample.

12. The device of claim 1, wherein the magnetic field sensor is adapted to detect analytes from greater than 1 μm to about 5,000 μm from the magnetic field sensor.

13. The device of claim 1, wherein the one or more magnets are adapted to effect mixing of the sample.

14. The device of claim 1, wherein two or more magnets are arranged at substantially opposite ends of the channels or sample wells.

15. The device of claim 14, wherein magnets at opposite ends of the channels or sample wells are activated alternately to effect mixing.

* * * * *